United States Patent [19]

Hamilton, Jr. et al.

[11] Patent Number: 4,996,386
[45] Date of Patent: Feb. 26, 1991

[54] CONCURRENT ISOMERIZATION AND DISPROPORTIONATION OF OLEFINS

[75] Inventors: David M. Hamilton, Jr., Houston; Richard A. Kemp, Stafford, both of Tex.

[73] Assignee: Shell Oil Company, Houston, Tex.

[21] Appl. No.: 454,244

[22] Filed: Dec. 21, 1989

[51] Int. Cl.$^5$ ............................ C07C 6/00; C07C 5/23
[52] U.S. Cl. ...................................... 585/646; 585/666; 585/670
[58] Field of Search ...................... 585/646, 666, 670

[56] References Cited

U.S. PATENT DOCUMENTS

| 3,261,879 | 7/1966 | Banks | 260/683 |
|---|---|---|---|
| 3,340,322 | 5/1967 | Heckelsberg | 260/683 |
| 3,637,892 | 1/1972 | McGrath et al. | 260/683 D |
| 3,726,938 | 4/1973 | Berger | 260/683 D |
| 3,760,026 | 9/1973 | Reusser et al. | 260/683 D |
| 3,786,112 | 1/1974 | Reusser et al. | 260/683 D |
| 3,792,108 | 2/1974 | Arganbright | 260/683 D |
| 3,872,180 | 3/1975 | Nakatomi et al. | 260/683 D |
| 3,933,974 | 1/1976 | Winquist | 423/118 |
| 3,966,883 | 6/1976 | Vaughan et al. | 423/329 |
| 4,000,248 | 12/1976 | Martin | 423/329 |
| 4,017,590 | 4/1977 | Cormier | 423/329 |
| 4,180,524 | 12/1979 | Reusser et al. | 585/644 |
| 4,251,499 | 2/1981 | Nanne et al. | 423/329 |
| 4,335,019 | 6/1982 | Bowes et al. | 502/66 |
| 4,343,692 | 8/1982 | Winquist | 208/111 |
| 4,727,203 | 2/1988 | Hamilton | 585/670 |
| 4,749,819 | 6/1988 | Hamilton | 585/666 |
| 4,754,099 | 6/1988 | Kemp et al. | 585/646 |

FOREIGN PATENT DOCUMENTS 1128091 3/1966 United Kingdom .
1205677 9/1970 United Kingdom .

OTHER PUBLICATIONS

"Composition and Catalytic Properties of Synthetic Ferrierite", Journal of Catalysis, 35, pp. 256-272 (1974).

Primary Examiner—Curtis R. Davis
Attorney, Agent, or Firm—Pamela J. McCollough

[57] ABSTRACT

This invention relates to a process for the concurrent isomerization and disproportionation of hydrocarbon olefins by contacting said hydrocarbon at disproportionation conditions with a catalyst prepared by incorporating a ferrierite compound and a metals solution containing cobalt and an element selected from the group consisting of molybdenum and tungsten into an alumina hydrogel.

18 Claims, No Drawings

CONCURRENT ISOMERIZATION AND DISPROPORTIONATION OF OLEFINS

FIELD OF THE INVENTION

This invention relates to a process for the concurrent isomerization and disproportionation of olefinic hydrocarbons utilizing a hydrogel-derived catalyst.

BACKGROUND OF THE INVENTION

Reactions of olefinic molecules in the presence of metal-containing catalysts to produce other olefinic molecules are known in the art as "disproportionation" reactions. A typical olefin disproportionation process is illustrated by U.S. Pat. No. 3,261,879, issued July 19, 1966, to Banks, wherein two similar non-symmetrical molecules of an olefin react in the presence of certain catalysts to produce one olefin of a higher carbon number and one olefin of a lower carbon number such as, for example, propylene disproportionation by the process of U.S. Pat. No. 3,261,879 to produce ethylene and butylenes.

As used in this application, disproportionation process means the conversion of olefinic hydrocarbons into similar olefinic hydrocarbons of higher and lower numbers of carbon atoms per molecule. Where the reactant comprises 1- or 2-olefins having relatively long chains, a mixture of products is obtained comprising primarily olefins having both a larger and a smaller number of carbon atoms than the feed olefin but also including other disproportionated products, for example, saturated hydrocarbons, and other converted and unconverted material. Such an operation is useful in many instances. For example, a more plentiful hydrocarbon can be converted to a less plentiful and therefore more valuable hydrocarbon. One instance of such a conversion occurs when the process of this invention is used to convert both higher and lower molecular weight olefins to olefins in the $C_{10}$–$C_{16}$ range, a range of olefins especially suitable for the manufacture of detergents. Another instance of a disproportionation reaction having considerable value is the disproportionation of propylene to produce ethylene and butene.

A variety of catalysts have been employed for conducting disproportionation reactions, such as those disclosed in U.S. Pat. No. 3,340,322, issued Sept. 5, 1967., U.S. Pat. No. 3,637,892, issued Jan. 25, 1972; U.S. Pat. No. 3,760,026, issued Sept. 18, 1973; U.S. Pat. No. 3,792,108, issued Feb. 12, 1974., U.S. Pat. No. 3,872,180, issued Mar. 18, 1975., and British Pat. Specification No. 1,128,091, published Mar. 16, 1966.

It is also known that the presence of a catalyst which possesses double bond isomerization activity in a disproportionation process is advantageous because it increases the rate of conversion and makes possible the production of a wider range of symmetrical olefins such as butene-2. In addition, the isomerization activity permits the exhaustive cleavage of high molecular weight monoolefins with ethylene to lower molecular weight monoolefins such as propylene and isobutene. British Pat. No. 1,205,677, published Sept. 16, 1970, provides a catalyst which comprises an olefin disproportionation component and a Group VIII noble metal double bond isomerization component, i.e., palladium, platinum or ruthenium. Another catalyst system which accomplishes the same results is obtained by physically mixing catalytic magnesium oxide with tungsten oxide on silica catalyst. Other catalysts which have been developed include those obtained by copromoting an olefin disproportionation catalyst such as tungsten oxide on silica with minor amounts of the oxides of niobium, tantalum or vanadium to provide the double bond isomerization activity.

U.S. Pat. No. 3,786,112 discloses a catalyst comprising a physical mixture of an olefin disproportionation catalyst and a double bond isomerization catalyst wherein the double bond isomerization catalyst has been treated with an alkali metal or alkaline earth metal compound.

U.S. Pat. No. 4,180,524 discloses a single catalyst composition containing a support, uranium and at least one of molybdenum, tungsten or rhenium, which provides double bond isomerization activity as well as olefin disproportionation activity.

The catalysts in the above references are generally prepared according to conventional methods such as impregnation, wherein a carrier is impregnated with a solution of metals., co-precipitation, wherein a carrier compound and metals are simultaneously precipitated; or co-mulling, wherein dry powders are mixed with a suitable extrusion aid such as water and extruded. U.S. Pat. No. 4,754,099 is directed to a disproportionation process utilizing a cobalt/molybdenum hydrogel-derived catalyst.

The catalyst in the above references for isomerization and combined isomerization/disproportionation have either basic or neutral isomerization components. It has been found in the present invention that an acidic isomerization component in combination with a disproportionation component can be used for concurrent isomerization/disproportionation with a low side-product make, thus resulting in a greater quantity of useful olefins.

SUMMARY OF THE INVENTION

The present invention relates to a process for the concurrent isomerization and disproportionation of olefinic hydrocarbons which comprises contacting said olefinic hydrocarbons with a catalyst comprising cobalt, an element selected from the group consisting of molybdenum, tungsten and mixtures thereof, and a ferrierite compound incorporated into an alumina hydrogel which is then processed to prepare the catalyst.

It has been found that an acidic hydrogel-derived catalyst shows substantially improved branched product yields, i.e., less branching, in a concurrent olefin isomerization and disproportionation process when compared to conventionally prepared catalyst useful for disproportionation. The hydrogel-derived catalyst in this invention can be prepared by adding catalytically active metals to an alumina hydrogel as dry salts, solutions, or a mixture of dry salts and solutions. In an olefin production process combining the steps of oligomerization, isomerization and disproportionation such as that disclosed in U.S. Pat. No. 3,726,938, issued to Berger, it is preferred to use catalysts prepared according to the instant invention in the disproportionation zone. Another advantage of the hydrogel route is a lower manufacturing cost due to reduced product yield loss and reduced number of heating steps.

DESCRIPTION OF THE PREFERRED EMBODIMENTS

In the process of the instant invention, the concurrent isomerization and disproportionation of an olefinic hydrocarbon is accomplished by contacting the olefinic hydrocarbon with a catalyst prepared by incorporating cobalt, an element selected from the group consisting of molybdenum, tungsten and mixtures thereof, and a ferrierite compound into an alumina hydrogel and subsequently processing the hydrogel to prepare the catalyst.

Olefins which are subjected to isomerization and disproportionation according to the process of this invention include $C_3^{31}$ olefinic hydrocarbons or $C_3^-$ internal olefins in combination with ethylene. A useful group of feed materials are olefinic hydrocarbons having carbon numbers ranging from $C_2$ to about $C_{100}$ and mixtures thereof, preferably from $C_2$ to about $C_{60}$ and mixtures thereof, and more preferably linear olefinic hydrocarbons having carbon numbers ranging from about $C_4$ to about $C_{40}$ and mixtures thereof. Examples of compounds most suitable for disproportionation according to this invention are acyclic 1- and 2-alkenes, and alkyl and aryl derivatives thereof having from 3 to 20 carbon atoms per molecule. Some specific examples of such olefins are propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, and 3-heptene. Higher disproportionation conversions and wider product distributions are obtained at comparable reaction times with 1-olefins than with 2-olefins. 3-olefins are disproportionated at still lower rates.

The feed should be essentially free of impurities which adversely affect the reaction. A subsequent reactivation of the catalyst to remove the effect of such impurities can be made repeatedly by heat treatment with air, using an inert gas to control burn-off temperature.

The catalyst of this invention is prepared by incorporating cobalt, an element selected from the group consisting of molybdenum, tungsten and mixtures thereof, and a ferrierite compound into an alumina hydrogel prepared by titrating an aqueous solution of an acid aluminum compound and an aqueous solution of a basic aluminum compound and subsequently calcining the hydrogel to prepare the catalyst.

The alumina hydrogel can be prepared by titrating an aqueous solution of one or more aluminum salt(s) with an appropriate acidic or basic material or solution to cause precipitation of the alumina gel. One skilled in the art will recognize that the alumina gel can be prepared by titrating an acidic aluminum salt such as, for example, aluminum sulfate, aluminum nitrate or aluminum chloride, in aqueous solution with a basic precipitating reagent such as, for example, sodium hydroxide or ammonium hydroxide, or, by titrating an alkali metal aluminate such as, for example, sodium aluminate or potassium aluminate, in aqueous solution with an acidic precipitating reagent such as, for example, hydrochloric acid or nitric acid. One skilled in the art will recognize that the adjustment of the pH of an aluminum-containing solution to between about 5.5 and about 10.0 will result in precipitation of the aluminum as aluminum hydroxide or hydrated aluminum oxide.

In a preferred embodiment, the alumina hydrogel is prepared by titrating an aqueous solution of an alkali metal aluminate and an aqueous solution of an acid aluminum salt to cause precipitation of the alumina gel. Suitable acidic aluminum salts include aluminum sulfate, aluminum nitrate and aluminum chloride. A preferred species is aluminum sulfate. Suitable alkali metal aluminates are sodium aluminate and potassium aluminate. The precipitation can be carried out by adding an aqueous solution of the basic aluminum species to an aqueous solution of the acidic aluminum species or the procedure can be reversed by adding an aqueous solution of the acidic aluminum species to an aqueous solution of the basic aluminum species (referred to as "sequential precipitation"). Preferably, the precipitation in the instant invention is carried out by simultaneously adding the acid aluminum species and the basic aluminum species to cause precipitation of the hydrogel (referred to as "simultaneous precipitation"). The maximum rate of addition of the acid aluminum species and the basic aluminum species is fixed by the rate at which the two streams can be mixed and the pH and temperature of the system can be effectively controlled.

The temperature and pH of the precipitation are important variables in the preparation of the aluminas into which metals can be incorporated to form catalysts with desirable physical qualities. One skilled in the art would recognize that changes in precipitation temperatures and pHs result in changes in porosities. The optimal temperatures and pHs for the precipitation of the aluminas can be determined with a minimal amount of routine experimentation. In the instant invention, a precipitation temperature typically ranges from about 20° C. to about 90° C., preferably from about 50° C. to about 85° C., more preferably from about 55° C. to about 65° C., and a precipitation pH typically ranges between about 5.5 and about 10.0, preferably between about 5.5 and about 8.0, and more preferably between about 6.0 and about 7.5. The length of time required for the precipitation step is typically from about 15 minutes to about 45 minutes. The period of time for the precipitation should be sufficiently long for adequate mixing of the materials, but not long enough for enhanced particle growth to occur.

After the precipitation step is completed, the pH of the slurry is adjusted by the addition of the basic aluminate solution to fall in the range from about 8.0 to about 12.0, preferably about 9.0 to about 11.0, most preferably about 9.5 to about 10.5, and aged at a temperature in the range from about 20° C. to about 90° C., preferably about 50° C. to about 85° C. for at least 15 minutes. An upper limit on the length of time for aging is not critical and is normally determined by economical considerations. Aging times will typically range from about 0.1 to about 10 hours, preferably from about 0.25 to about 5 hours, and more preferably from about 0.25 to about 1 hour. In general, aluminas with acceptable properties are produced by holding the aging temperature equal to the precipitation temperature.

After aging, the slurry is washed and filtered in routine fashion to remove substantially all of the water-soluble salts formed during the precipitation of the hydrogel. The preferred solvent for washing is water although other solvents such as lower alkanols may be utilized.

After washing, the ferrierite compound and the metals are incorporated into the hydrogel. The ferrierite compound is typically a synthetic ferrierite which is usually prepared as ammonium aluminosilicate or as an alkali metal aluminosilicate. The alkali metal ion is typically sodium or potassium. The ferrierite may also be converted to the acid form by calcination or by contacting the alkali metal aluminosilicate with a dilute acid such as 3 N or 6 N hydrochloric acid. In a preferred embodiment, the ferrierite is added to the hydrogel as ammonium ferrierite.

The synthetic ferrierite itself may be prepared by a variety of processes. These include, for example, the process described in U.S. Pat. Nos. 3,966,883, 4,000,248 and 4,017,590. A particularly useful process for preparing synthetic ferrierite is described in U.S. Pat. Nos. 3,933,974 and 4,343,692, which disclosures are herein incorporated by reference. Other processes are described in U.S. Pat. No. 4,251,499 and Kibby et al, "Composition and Catalytic Properties of Synthetic Ferrierite", *Journal of Catalysis*, 35, pages 256–272 (1974).

The prominent structural features of synthetic ferrierite have been found by X-ray crystal structure determination to be parallel channels in the aluminosilicate framework. The term "ferrierite compound", as used herein, referes to a two dimensional zeolite consisting of intersecting 8 and 10 ring channels. The larger 4.3 Å×5.5 Å ten ring channel parallels the c crystallographic axis, while the smaller 3.4 Å×4.8 Å eight ring channel parallels the b crystallographic axis. Practically speaking, the larger ten ring channel is the only diffusion path available to a molecule of any moderate size. Therefore, the channel system of ferrierite is essentially unidimensional due to practical considerations.

The ferrierite is typically added to the hydrogel in the form of a powder in an amount sufficient to yield a final catalyst having from about 1 percent by weight to about 35 percent by weight, preferably from about 2 by weight to about 25 percent by weight, and more preferably from about 5 percent by weight to about 15 percent by weight of ferrierite. The ferrierite may be added to the hydrogel prior to the addition of the metals, at the same time as the metals or after the metals have been added to the hydrogel.

One method for adding the metals to the hydrogel is a reslurry step in which the hydrogel is reslurried with a metals solution containing solubilized salts of cobalt and an element selected from the group consisting of molybdenum, tungsten and mixtures thereof, sufficient to deposit on the final catalyst from about 0.1 percent by weight to about 5 percent by weight cobalt and from about 5 percent by weight to about 18 percent by weight molybdenum or about 8 percent by weight to about 32 percent by weight tungsten. When mixtures of molybdenum and tungsten are utilized, the final catalyst contains from about 5 percent by weight to about 32 percent by weight molybdenum and/or tungsten. The solution may, however, contain amounts of cobalt and molybdenum or tungsten in excess of that required to deposit the aforesaid amounts of metals, which excess may be removed by washing or other techniques following the reslurry step. A typical metals solution can be prepared by combining a molybdenum solution with a cobalt solution.

The cobalt solution consists of cobalt salts dissolved in water. A wide range of cobalt compounds are suitable, such as cobalt nitrate, cobalt hydroxide, cobalt acetate, cobalt oxalate, or cobalt oxide. The preferred cobalt compound is cobalt nitrate.

The molybdenum solution consists of a water-soluble source of molybdenum oxide such as ammonium heptamolybdate or ammonium dimolybdate dissolved in water. Hydrogen peroxide may also be used to aid in solution preparation in some cases. Optionally, the molybdenum solution consists of adding hydrogen peroxide to the solution in the range of about 0.1 to about 1.0 mole of hydrogen peroxide per mole of molybdenum. Optionally, a suitable soluble amine compound such as monoethanolamine, propanolamine or ethylenediamine may be added to the molybdenum solution in order to aid in stabilization of the solution.

The tungsten solution typically consists of ammonium metatungstate dissolved in water. A preferred method for preparing the tungsten solution consists of adding hydrogen peroxide to the solution in the range of about 0.1 to about 1.0 mole of hydrogen peroxide per mole of tungsten. In addition, a suitable soluble amine compound such as monoethanolamine, propanolamine or ethylenediamine may be added to the tungsten solution in order to aid in stabilization of the solution.

An alternative method for incorporating the metals into the hydrogel is to add dry, water-soluble metal salts of cobalt, a heavy metal selected from the group consisting of molybdenum, tungsten and mixtures thereof, and mix until dissolution and adsorption of the metal salts onto the gel is substantially complete. The metal salts of cobalt, molybdenum and/or tungsten are added to the hydrogel in amounts sufficient to incorporate into the final catalyst from about 0.1 percent by weight to about 5 percent by weight cobalt and from about 5 percent by weight to about 18 percent by weight molybdenum or about 8 percent by weight to about 32 percent by weight tungsten. When mixtures of molybdenum and tungsten are utilized, the final catalyst contains about 5 percent by weight to about 32 percent by weight molybdenum and/or tungsten.

Cobalt is added to the hydrogel in the form of dry, water-soluble cobalt nitrate, cobalt hydroxide, cobalt acetate, cobalt oxalate or cobalt oxide, with cobalt nitrate being preferred. Molybdenum is generally added to the hydrogel as a dry, water-soluble source of molybdenum such as ammonium heptamolybdate or ammonium dimolybdate. Tungsten is typically added to the hydrogel as ammonium metatungstate.

A preferred method of mixing the dry metal salts of cobalt and molybdenum and/or tungsten with the hydrogel consists of adding hydrogen peroxide to the mixture of dry metal salts and hydrogel in an amount ranging from about 0.1 to about 1.0 mole of hydrogen peroxide per mole of molybdenum and/or tungsten. Optionally, a suitable amine compound such a monoethanolamine, propanolamine or ethylenediamine may be added to the mixture of dry metal salts and hydrogel in order to aid in stabilization of the mixture of the metal salts and the hydrogel.

The dry metals salts of cobalt, molybdenum and/or tungsten are typically added to the hydrogel in the form of finely divided particles which are generally 100 mesh or less in size. While particle size is not critical and larger particle sizes may be utilized, it is economically advantageous to use particles which are 100 mesh or less in size.

It is also within the scope of this invention to combine the two methods described above for adding the metals to the hydrogel. For example, one metal may be added to the hydrogel as a dry salt and another added in the form of a solution. Various permutations of this combination of dry salts additions and metals solutions additions would be obvious to one skilled in the art.

The temperature and pH of the step in which the ferrierite and the metals solutions and/or the dry metal salts are mixed with the hydrogel are important variables in the preparation of hydrogel-derived catalysts which have acceptable densities and porosities. The mixing of the hydrogel with the ferrierite and the metals solution or the dry metal salts is typically carried out at a pH in the range between about 4.0 and about 10.0 and a temperature in the range between about 25° C. and about 100° C., until incorporation of the ferrierite and the metals salts into the gel is sufficient to yield a final calcined catalyst having from about 0.1 percent by weight to about 5 percent by weight cobalt, from 8 percent by weight to about 32 percent by weight heavy metal selected from the group consisting of molybdenum, tungsten and mixtures thereof, and from about 1 percent by weight to about 35 percent by weight ferrierite. Typically, the times for mixing the hydrogel, the ferrierite and the metals will range from about 0.5 to about 2 hours. Optionally, the resulting material can be washed to remove unadsorbed metals and filtered in routine fashion.

Following the addition of the ferrierite and the metals to the hydrogel, the resulting material is processed in one of many routine methods to produce a finished catalyst. The material may be extruded and then dried and calcined, dried, mulled with addition of water, extruded or pelletized and calcined, or partially dried, extruded or pelleted, dried more completely and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

In a preferred embodiment, the material is extruded and then dried. Alternatively, the material may be extruded after drying to the proper loss on ignition (LOI). However, to facilitate extrusion, organic binders and/or lubricants may be added prior to extrusion.

After drying, the material is calcined to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently the calcining and/or burn-out steps are combined using an oxygen-containing atmosphere.

Certain other processing steps may be incorporated into the above-described procedure without deviating from the scope and intent of this invention. For example, an intensive mixer-muller can be used to process the material prior to extrusion. In a preferred embodiment, the material is subjected to shearing prior to drying and calcining in order to produce a stiffened hydrogel composition. The shearing of the hydrogel particles is accomplished by passing the hydrogel through a homogenizer such as, for example, a spring-loaded homogenization valve. The extent of shearing can be defined numerically by passing the hydrogel through a spring-loaded homogenization valve. A suitable degree of shear will normally be produced by a pressure drop in the range of from about 500 pounds per square inch to about 8,000 pounds per square inch, preferably from about 2,000 pounds per square inch to about 7,000 pounds per square inch, on an ordinary spring-loaded homogenizer such as, for example, a Gaulin 15 gallons per hour, 8,000 pounds per square inch Laboratory homogenizer. Shearing can also be effected by other means such as, for example, by use of a high-speed blender, but a homogenizer is preferred for continuous processing. The proper degree of shear in any event is that amount which produces an extrudate of the hydrogel which will not deform substantially under its own weight as formed. Thus, the extrudate formed prior to drying and calcining will retain its shape and enable the drying and calcining steps to be carried out without substantial change in shape. After subjecting the hydrogel to shearing, the resulting material can then be readily extruded through a manifold nozzle system.

The final catalysts are typically found to have surface areas greater than about 275 $m^2/g$. In general, the metals contents of the final catalysts range from about 0.1 percent by weight to about 5 percent by weight cobalt, preferably from about 2.5 percent by weight to about 4 percent by weight cobalt, and from about 8 percent by weight to about 18 percent by weight, preferably from about 10 percent by weight to about 14 percent by weight molybdenum or about 10 percent by weight to about 32 percent by weight, preferably from about 18 percent by weight to about 26 percent by weight tungsten. The catalyst typically contains from about 1 percent by weight to about 35 percent by weight, preferably from about 2 percent to about 25 percent by weight ferrierite.

The process of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about 10° C. to about 350° C. and at pressures in the range of about 50 psig to about 500 psig. The disproportionation reaction is usually effected in a liquid phase in the presence of a small amount of ethylene and if desired, liquid reaction diluents are utilized. Examples of suitable diluents are hydrocarbons free from aliphatic unsaturation, such as acyclic or alicyclic alkanes of from 6 to 12 carbon atoms, i.e. hexane, isooctane and cyclohexane. Also exemplary would be monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst, which is influenced by surface area, promoter concentration, activation temperature, etc. In general, the distribution of products is not drastically altered by variation in contact time. Shorter contact times are usually associated with higher temperatures, but, when larger amounts of higher molecular weight products are desired, a suitable combination of contact time and temperature is selected. With proper selection of conditions and contact times, very high efficiency of conversion to desired products can be obtained.

In this application, space rates are given in WHSV (weight hourly space velocity, weight of reactant feed per weight of catalyst per hour).

With a fixed bed reactor, continuous flow operation at pressures in the range of about 50 psig to about 500 psig, preferably about 150 psig to about 250 psig, with catalysts having densities ranging from about 0.5 gram per cc to about 1.0 gram per cc and surface areas greater than about 200 $m^2/g$, and at temperatures in the range of about 10° C. to about 350° C., preferably about 100° C. to about 250° C., weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst. The higher space velocities in general are associated with higher reaction temperatures.

The catalyst of the present invention is advantageous with respect to a catalyst in which the olefin feed is only disproportionated rather than isomerized and disproportionated concurrently in that a different mixture of product olefins is obtained. The ability to shift the mixture of product olefins is particularly useful in maximizing the economic return from any given olefin feedstock.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

ILLUSTRATIVE EMBODIMENTS

Catalyst Preparation

Catalyst A 101.3 kilograms of aluminum sulfate solution was prepared by solubilizing 11.3 kilograms of gibbsite (alpha-alumina trihydrate, 34% LOI) in 90.0 kilograms of 27% sulfuric acid at a temperature slightly above 100° C. The solution was allowed to cool to 60° C. prior to use. 76.6 kilograms of sodium aluminate solution were prepared by solubilizing 28.3 kilograms of gibbsite (alpha-alumina trihydrate, 34% LOI) in 48.3 kilograms of 36% sodium hydroxide at a temperature slightly above 115° C. This solution was also allowed to cool to 60° C. prior to use. These two solutions were metered under computer control into a precipitation vessel containing deionized water heel (121 kilograms) held at 60° C., maintaining a constant pH of 7.0 and a temperature of 60° C. The precipitation duration was fixed at 15 minutes. After the precipitation step was complete excess sodium aluminate solution (8.4 kilograms) was added to the slurry to raise the pH to the desired aging pH of 10.0. Total solution quantities used: acid —41.0 kilograms, base —33.7 kilograms. The slurry was aged for one hour at the elevated pH. The slurry was then filtered in a single step on a 1'×10' horizontal belt vacuum filter and washed with deionized water. The resulting alumina hydrogel had a water content of 85.6%, basis dry weight of alumina.

The filtered almina hydrogel (4000 grams, or 576.4 grams of dry weight alumina) was agitated with a mixer until it liquefied. To this hydrogel was added cobalt nitrate (119.6 grams), ammonium ferrierite (59.6 grams), and ammonium heptamolybdate (112.7 grams) at room temperature. The pH of the slurry was 6.2. After reaction for two hours at room temperature the catalyst hydrogel slurry was passed through a Gaulin Model 15M Lab Homogenizer using a pressure drop of 6000 psi. The stiffened material was extruded through a manifold/extruder nozzle system. The material was dried at 150° C. for several hours, followed by calcination in air via a 30/minute ramp from 120° C. to 150° C. The material was held at 500° C. for two hours. The properties of the catalyst are listed in Table I.

Catalyst B

Catalyst B was prepared using a conventional dry pore volume impregnation technique. A solution suitable for impregnating 75 grams of calcined alumina support with a pore volume of 0.69 cc/g was prepared as follows. An impregnation solution was made by combining 5.78 grams of cobalt nitrate, 12.86 grams of ammonium dimolybdate and enough 24% aqueous ammonia to bring the solution to a total volume of 51 milliliters. After adding the entire solution to the alumina support in several small portions with intermediate agitations, the impregnated support was dried overnight at 150° C. and calcined in air for 2 hours at 450° C. The properties of the catalyst are listed in Table I.

Catalyst Testing

Catalysts A and B were each tested utilizing the following procedure. Twenty ccs of 16-45 mesh catalyst particles diluted 1/1 with 80 mesh SiC are charged to a stainless steel reactor to obtain a bed length of 8 inches. The catalyst is heated at a temperature of 550° C. under flowing nitrogen for 12 hours to remove any residual water from the catalyst. The catalyst is then cooled to 250° F. and feed is introduced at a weight hourly space velocity (WHSV) of about 1.0. The feed for these reactions is an equilibrium mixture of decenes prepared by the isomerization of 1-decene. The feed contains approximately 1.5% branched decenes. The results of catalyst testing are presented in Table II.

As mentioned previously, hydrogel catalysts prepared by the process of the instant invention have improved selectivity to linear olefins, higher conversion rates and a wider range of reaction products than conventionally prepared disproportionation catalysts. Values in the "Product Branching" section in Table II represent the relative amount of branched olefins in the product stream and are reported relative to the conventionally prepared catalyst, which is shown as 1.00. A value of less than 1.00 would indicate fewer branched olefins in the product stream and thus a more selective and hence more desirable catalyst. Values in the Carbon Number Distribution Section of Table II are reported in normalized weight percent. It is clear from the data in Table II that shifts in the overall product distribution are seen when Catalyst A, the mixed isomerization/disproportionation catalyst prepared according to the invention, is used. In addition, when Catalyst A according to the invention is utilized, less of the more valuable linear olefins are converted into branched olefins, which are less valuable and thus, undesired side products.

TABLE I

| Catalyst Properties | | |
|---|---|---|
| Catalyst | A | B |
| % wt. Molybdenum[a] | 8.1 | 8.1 |
| % wt. Cobalt[b] | 3.2 | 3.2 |
| % wt. Ferrierite[c] | 8.4 | — |
| Surface Area[d] $m^2/gm$ | 395 | 250 |

[a] Weight percent determined by neutron activation analysis or atomic absorption spectroscopy.
[b] Weight percent determined by neutron activation analysis or atomic absorption spectroscopy.
[c] Weight percent determined by neutron activation analysis or atomic absorption spectroscopy.
[d] BET, by nitrogen adsorption/desorption, Micromeritics Digisorb 2500 Instrument.

TABLE II

| Catalyst Test Results | | |
|---|---|---|
| Catalyst | A | B |
| $C_{10}$ Feed | Iso. $C_{10}$ | Iso. $C_{10}$ |
| Reaction Temperature, °F. | 248 | 250 |
| Catalyst Volume, cc | 20 | 20 |
| Catalyst Weight, gm | 14.5 | 13.4 |
| WHSV | 1.1 | 1.5 |
| Product Branching | 0.21 | 1.00 |
| Carbon Number Distribution | | |
| $C_2$ | 0.000 | 0.000 |
| $C_3$ | 0.054 | 0.027 |
| $C_4$ | 1.293 | 0.743 |
| $C_5$ | 2.582 | 1.646 |
| $C_6$ | 5.056 | 3.574 |
| $C_7$ | 7.561 | 5.693 |
| $C_8$ | 10.015 | 8.166 |
| $C_9$ | 11.203 | 10.542 |
| $C_{10}$ | 13.756 | 13.817 |
| $C_{11}$ | 10.578 | 13.053 |
| $C_{12}$ | 9.603 | 12.281 |
| $C_{13}$ | 8.451 | 10.345 |
| $C_{14}$ | 7.221 | 8.091 |
| $C_{15}$ | 5.461 | 5.462 |
| $C_{16}$ | 3.709 | 3.290 |
| $C_{17}$ | 1.841 | 1.454 |
| $C_{18}$ | 0.901 | 0.721 |
| $C_{19}$ | 0.419 | 0.414 |
| $C_{20}$ | 0.177 | 0.245 |
| $C_{21}$ | 0.079 | 0.243 |
| $C_{22}$ | 0.029 | 0.057 |
| $C_{23}$ | 0.013 | 0.063 |
| $C_{24}$ | 0.000 | 0.026 |
| $C_{25}$ | 0.000 | 0.018 |
| $C_{26}$ | 0.000 | 0.012 |
| $C_{27}$ | 0.000 | 0.011 |
| $C_{28}$ | 0.000 | 0.007 |

What is claimed is:

1. A process for the concurrent isomerization and disproportionation of olefinic hydrocarbons having carbon numbers ranging from $C_2$ to about $C_{100}$ which comprises contacting said olefins with a catalyst prepared by incorporating cobalt, a heavy metal selected from the group consisting of molybdenum, tungsten and mixtures thereof, and a ferrierite compound into an alumina hydrogel and subsequently calcining to prepare said catalyst.

2. The process of claim 1 wherein said catalyst contains from about 0.1 percent by weight to about 5 percent by weight cobalt and from about 8 percent by weight to about 32 percent by weight heavy metal.

3. The process of claim 2 wherein said catalyst contains from about 2.5 percent by weight to about 4 percent by weight cobalt and from about 8 percent by weight to about 18 percent by weight molybdenum.

4. The process of claim 1 wherein said catalyst contains from about 1 percent by weight to about 35 percent by weight ferrierite compound.

5. The process of claim 1 wherein said catalyst contains from about 2 percent by weight to about 25 percent by weight ferrierite compound.

6. The process of claim 1 wherein said olefinic hydrocarbons have carbon numbers ranging from $C_2$ to about $C_{60}$.

7. The process of claim 1 wherein said process is carried out at a temperature in the range of from about 10° C. to about 350° C. and a pressure in the range of from about 50 psig to about 500 psig.

8. A process for the concurrent isomerization and disproportionation of olefinic hydrocarbons having carbon numbers ranging from $C_2$ to about $C_{100}$ which comprises contacting said olefinic hydrocarbons at disproportionation conditions with a catalyst prepared by a process which comprises:

(a) precipitating an aqueous solution of one or more aluminum salt(s) by adjusting the pH of said solution to a range between about 5.5 and about 10.0 at a temperature in the range between about 20° C. and about 90° C., (b) aging the precipitate at a temperature ranging from about 20° C. to about 90° C. for at least about 15 minutes at a pH ranging from about 8.0 to about 12.0, (c) washing the precipitate, (d) mixing the precipitate with a ferrierite compound and solubilized salts of cobalt and a heavy metal selected from the group consisting of molybdenum, tungsten and mixtures thereof, at a pH in the range between about 4.0 and about 10.0 and a temperature in the range between about 25° C. and about 100° C. until adsorption of the metal salts onto the gel is sufficient to yield a final catalyst having from about 1 percent by weight to about 5 percent by weight cobalt, from about 8 percent by weight to about 32 percent by weight heavy metal, and from about 1 percent by weight to about 35 percent by weight ferrierite, (e) extruding the product of step (d), and (f) drying and calcining the product of step (e) at a temperature ranging from about 300° C. to about 900° C.

9. The process of claim 8 wherein the precipitation is carried out at a pH in the range between about 5.5 and about 8.0.

10. The process of claim 8 wherein the precipitation is carried out at a temperature between about 50° C. and about 85° C.

11. The process of claim 8 wherein the aging pH is in the range between about 9.0 and about 11.0.

12. The process of claim 8 wherein step (d) is carried out at a pH in the range between about 4.0 and about 8.0.

13. The process of claim 8 wherein said heavy metal is molybdenum.

14. The process of claim 13 wherein said catalyst contains from about 2.5 percent by weight to about 4 percent by weight cobalt and from about 8 percent by weight to about 18 percent by weight molybdenum.

15. The process of claim 8 wherein said catalyst contains from about 2 percent by weight to about 25 percent by weight ferrierite compound.

16. The process of claim 15 wherein said catalyst contains from about 5 percent by weight to about 15 percent by weight ferrierite compound.

17. The process of claim 8 wherein said olefinic hydrocarbons have carbon numbers ranging from $C_2$ to about $C_{60}$.

18. The process of claim 8 wherein said process is carried out at a temperature of from about 10° C. to about 350° C. and a pressure of from about 50 psig to about 500 psig.

* * * * *